United States Patent [19]
Hilger et al.

[11] Patent Number: 6,143,275
[45] Date of Patent: Nov. 7, 2000

[54] TYPE $S_3N_2$ CHELATORS FOR RADIOACTIVE ISOTOPES, THEIR METAL COMPLEXES AND THEIR DIAGNOSTIC AND THERAPEUTICAL USE

[75] Inventors: Christoph-Stephan Hilger; Ludger Dinkelborg; Wolfgang Kramp, all of Berlin; Hans-Martin Schier, Strausberg, all of Germany

[73] Assignee: Institut fur Diagnostikforschung GmbH an der Freien Universitat Berlin, Berlin, Germany

[21] Appl. No.: 08/530,342

[22] PCT Filed: Mar. 29, 1994

[86] PCT No.: PCT/DE94/00370

§ 371 Date: Mar. 8, 1996

§ 102(e) Date: Mar. 8, 1996

[87] PCT Pub. No.: WO94/22492

PCT Pub. Date: Oct. 13, 1994

[30] Foreign Application Priority Data

Mar. 31, 1993 [DE] Germany ............... 43 11 022

[51] Int. Cl.$^7$ ............ A61K 51/00; A61M 36/14
[52] U.S. Cl. ............ 424/1.69; 424/1.11; 424/1.65; 424/9.1; 534/14
[58] Field of Search ............ 424/1.11, 1.37, 424/1.19, 1.65, 1.53, 1.69, 9.1; 534/7, 10–16; 530/300, 324, 325, 326, 333, 338, 334, 327, 328, 329; 548/950, 400, 100; 546/1; 544/1; 540/450

[56] References Cited

FOREIGN PATENT DOCUMENTS

| | | |
|---|---|---|
| 0 063 946 A1 | 11/1982 | European Pat. Off. . |
| 0 089 143 A1 | 9/1983 | European Pat. Off. . |
| 0 173 424 A1 | 3/1986 | European Pat. Off. . |
| 0 188 256 A2 | 7/1986 | European Pat. Off. . |
| 0 247 866 A1 | 12/1987 | European Pat. Off. . |
| 0 250 013 A1 | 12/1987 | European Pat. Off. . |
| 0 299 795 A1 | 1/1989 | European Pat. Off. . |
| WO 92/19274 | 11/1992 | WIPO . |
| WO 93/15771 | 8/1993 | WIPO . |

OTHER PUBLICATIONS

Chemical Abstracts, vol. 118, No. 5, Feb. 1, 1993, Columbus, Ohio, US, abstract No. 33497.
Chemical Abstracts, vol. 119, No. 13, Sep. 27, 1993, Columbus, Ohio, US, abstract No. 139794.
Tetrahedron, vol. 38, No. 14, 1982, Oxford, GB, pp. 2055–2060, T. Lodi et al., 'Chiral Aminoacid Containing Acyclic Ligands–I. Syntheses and Conformations'.
Tetrahedron, vol. 38, No. 14, 1982, Oxford, GB, pp. 2061–2067, R. Marchelli et al., 'Chiral Aminoacid Containing Ligands–II. Complexation of Alkaline Earth Cations'.
Bioconjugate Chemistry, vol. 2, Sep. 1992, Washington, US, pp. 353–366, James P. Dizio et al., 'Progestin–Rhenium Complexes: Metal–Labeled Steroids With High Receptor Binding Affinity, Potential Receptor–Directed Agents For Diagnostic Imaging Or Therapy'

*Primary Examiner*—José G. Dees
*Assistant Examiner*—Dameron Jones
*Attorney, Agent, or Firm*—Wood, Phillips, VanSanten, Clark & Mortimer

[57] ABSTRACT

This invention relates to new bifunctional chelating agents with intermittent chalcogen atoms, pharmaceuticals containing these compounds, their use in radiodiagnostics and radiotherapy, and methods for the production of these compounds.

The compound according to the invention has the general formula (I)

$$M—L$$

wherein M represents a radionuclide of Tc or Re and L a ligand of the general formula (II)

$$B—CO—CR^1R^2—A—CR^3R^4—CO—D \qquad (II)$$

These new, bifunctional chelating agents with intermittent chalcogen atoms and their coupling products with compounds that accumulate specifically are suited for producing radiopharmaceuticals for diagnostic and therapeutic purposes.

36 Claims, 1 Drawing Sheet

(1 of 1 Drawing Sheet(s) Filed in Color)

TYPE S₃N₂ CHELATORS FOR RADIOACTIVE ISOTOPES, THEIR METAL COMPLEXES AND THEIR DIAGNOSTIC AND THERAPEUTICAL USE

TECHNICAL FIELD OF THE INVENTION

This invention relates to new bifunctional chelating agents with intermittent chalcogen atoms, pharmaceuticals containing these compounds, their use in radiodiagnostics and radiotherapy, and methods for the production of these compounds and pharmaceuticals.

BACKGROUND OF THE INVENTION

It has been known for a long time that complexing agents for radioactive isotopes or their complexes with radio-active metals can be applied in radiodiagnostics and radio-therapy. Technetium-99m is the most frequently used radio-nuclide in radiodiagnostics because it is particularly well suited for in-vivo applications due to its favourable physical properties (no corpuscular radiation, low half-life of 6.02 h, good detectability by 140 keV γ-radiation) as well as its low biological half-life and easy availability. The first step of forming complexes of technetium-99m is to gain pertechnetate from a nuclide generator; it is then converted to a lower oxidation number using appropriate reductants (such as $SnCl_2$, $S_2O_4^{2-}$, etc.). This oxidation number is stabilized by an appropriate chelating agent. As technetium may have several oxidation numbers (+7 to −1) which may vehemently alter its pharmacological properties by changing the charge of the complex, it is necessary to provide chelating agents or complex ligands for technetium-99m that are capable of binding technetium in a specific oxidation number safely, firmly and stably to prevent undesirable biodistribution due to in-vivo redox processes or release of technetium from the radiodiagnostic agent which would impede the safe diagnosis of the respective diseases.

For example, cyclic amines (Troutner, D. E. et al.: J. Nucl. Med. 21, 443 (1980)) are regarded as suitable complexing agents for technetium and rhenium isotopes but their disadvantage is that they are only capable of binding technetium-99m in sufficient quantities from a pH value >9. $N_2O_2$ systems (Pillai, M. R. A., Troutner, D. E. et al.: Inorg. Chem., 29, 1850 (1990)) are in clinical use. Non-cyclic $N_4$ systems such as HMPAO have the great disadvantage of low complex stability. Tc-99m-HMPAO has to be applied immediately after labelling due to its low stability (Ballinger, J. R. et al., Appl. Radiat. Isot. 42, 315 (1991); Billinghurst, M. W. et al., Appl. Radiat. Isot. 42, 607 (1991)) to keep the portion of decomposition products low which have different pharmacokinetic and excretion properties. Such radiochemical impurities make detection of the diseases to be diagnosed more difficult. Any coupling of these chelates or chelating agents with other substances that accumulate selectively in centres of diseases cannot be broken by simple means so that these normally spread unspecifically in the organism.

$N_2S_2$ chelating agents (Bormans, G. et al.: Nucl. Med. Biol., 17, 499 (1990)) such as ethylene dicysteine (EC; Verbruggen, A. M. et al.; J. Nucl. Med. 33, 551 (1992)) meet the requirement of sufficient stability of their respective technetium-99m complex but form radiodiagnostic agents of a purity greater than 690 only at pH values >9 of the complexing medium. $N_3S$ systems (Fritzburg, A.; EPA 0 173 424 and EPA 0 250 013) yield stable technetium-99m complexes but have to be heated up to temperatures of ca. 100° C. to insert the radionuclide.

Another disadvantage of $N_2S_2$ and $N_3S$ systems is that they are discharged too rapidly and without specific accumulation in the organism. Thus they are only used clinically, though to a limited extent, in renal function diagnostics. Their use is limited mainly because the demand has increased for substances that accumulate specifically in diseased tissues. This can be accomplished if one manages to link complexing agents easily with selectively accumulating substances while the latter retain their favourable complexing properties. But as it happens quite frequently that a certain reduction of complex stability is observed after coupling the complexing agent to such a molecule by means of one of its functional groups, previous approaches to coupling chelating agents with substances that accumulate selectively are hardly satisfactory because a quantity of the isotope that is not tolerable with a view to diagnostics is released in vivo from the conjugate (Brechbiel, M. W. et al.; Inorg. Chem. 1986, 25, 2772). It is therefore necessary to produce bifunctional complexing agents that have functional groups to bind the desired metallic ion and one (or several other) functional groups to bind the selectively accumulating molecule. Such bifunctional ligands allow specific, chemically defined bonding of technetium or rhenium isotopes to the most various biological materials even in cases in which pre-labelling is applied. Some chelating agents coupled with monoclonal antibodies (e.g. EP Appl. 0 247 866 and EP Appl. 0 188 256) or fatty acids (EP Appl. 0 200 492) have been described. But these were based on the $N_2S_2$ systems mentioned above which are hardly appropriate due to their low stability. As both the properties of the substances that accumulate selectively and the mechanisms of accumulation are quite varied, one should be able to vary the chelating agent meant for coupling to adapt it to the physiological requirements of its partner with regard to lipophilic or hydrophilic behaviour, membrane permeability or impermeability, etc.

SUMMARY OF THE INVENTION

It is therefore an object of this invention to provide stable complex compounds coupled with or capable of coupling with various compounds that accumulate selectively, and to provide such linkable chelating agents or complexes whose substituents show a wider range of chemical variation to be adaptable to the above requirements. It is another object of this invention to provide such compounds and pharmaceuticals containing these compounds, as well as methods for their production.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE PREFERRED EMBODIMENTS

Figure 1:
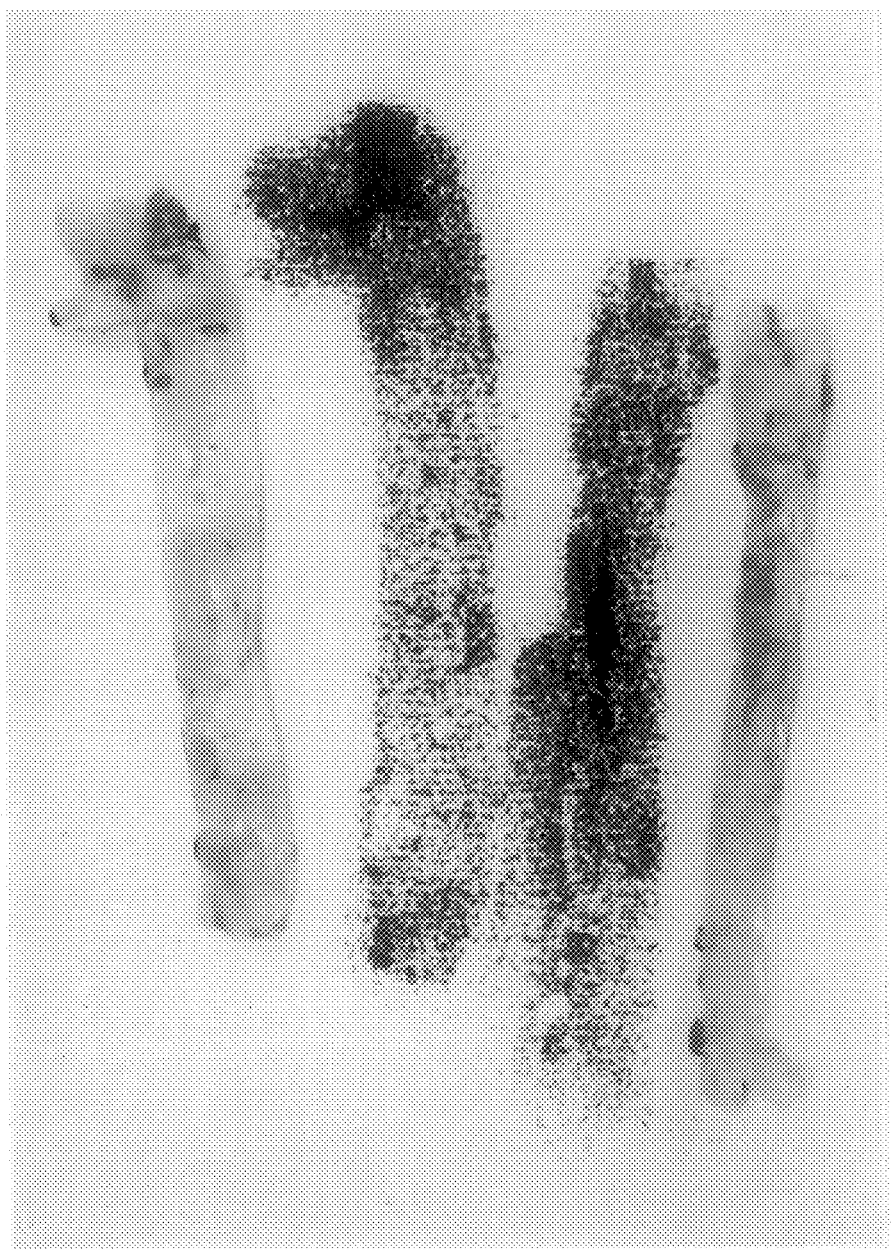
FIG. 1 illustrates a Sudan (III) staining and autoradiogram of the aorta of a WHHL rabbit.

This problem is solved by the invention, surprisingly, in that the new, uncommon, bifunctional chelating agents with intermittent chalcogen atoms and their coupling products with compounds that accumulate selectively are excellently suited for producing radiodiagnostic and radiotherapeutic agents.

The subject matter of this invention are compounds of the general formula (I)

$$M\text{---}L \qquad (I)$$

wherein

M represents a radionuclide of Tc or Re and L represents a ligand of the general formula (II)

$$B\text{---}CO\text{---}CR^1R^2\text{---}A\text{---}CR^3R^4\text{---}CO\text{---}D \qquad (II)$$

wherein

A represents an O, S, or Se chalcogen atom, $R^1$, $R^2$, $R^3$, and $R^4$ are same or different and represent a hydrogen atom and/or a branched or unbranched $C_1$–$C_6$ alkyl residue, B and D are same or different and represent a residue —NH—$CR^5R^6$ —$(CR^7R^8)_{n=1, 2}$—S—$R^9$, wherein $R^5$ and $R^6$ are same or different and represent a hydrogen atom or an unbranched, branched, cyclic, or polycyclic $C_1$–$C_{60}$ alkyl, alkenyl, polyalkenyl, alkynyl, polyalkynyl, aryl, alkylaryl, or arylalkyl residue which may optionally carry additional hydroxy, carboxy, aminocarbonyl, alkoxy-carbonyl, amino, aldehyde, oxo, oxy, or alkoxy groups containing up to 20 carbon atoms, and/or may optionally be interrupted, and/or replaced, by one or several heteroatoms from the series of O, N, S, P, As, Se, $R^7$ and $R^8$ are same or different and-represent a hydrogen atom and/or a branched or unbranched $C_1$–$C_6$ alkyl residue, $R^9$ represents a hydrogen atom, a branched or unbranched $C_1$–$C_6$ alkyl residue, or a sulfur protecting group, with $R^9$ and $R^5$, together with the groups that connect them, optionally forming a 4- to 8-membered ring which may optionally carry additional hydroxy, oxo, oxy, or alkoxy groups containing up to 6 carbon atoms.

Preferred compounds of the general formula (I) are characterized in that $R^1$, $R^2$, $R^3$, $R^4$, and $R^5$ are hydrogen atoms.

Particularly preferred compounds of the general formula (I) are characterized in that $R^1$, $R^2$, $R^3$, $R^4$, $R^5$, R7 and $R^8$ are hydrogen atoms.

Another object of this invention is related to the new, bifunctional ligands with intermittent chalcogen atoms of the general formula (II).

$$B\text{---}CO\text{---}CR^1R^2\text{---}A\text{---}CR^3R^4\text{---}CO\text{---}D \qquad (III)$$

wherein $R^1$, $R^2$, $R^3$, $R^4$, A, B, and D have the meanings specified above.

Such ligands according to the invention of the general formula (II) are preferred in which $R^1$, $R^2$, $R^3$, $R^4$, and $R^5$ are hydrogen atoms.

Particularly preferred ligands according to the invention are characterized in that $R^1$, $R^2$, $R^3$, $R^4$, $R^5$, $R^6$, $R^7$ and $R^8$ are hydrogen atoms.

Yet another object of this invention are conjugates containing compounds of the general formulae (I and/or II) and substances that accumulate selectively in diseased tissues, with a covalent bond existing between these substances, said bond being amidic if the substances contain carboxy or amino groups such as peptides, proteins, antibodies or their fragments, ester-like if the substances contain hydroxy groups such as fatty alcohols, and imidic if the substances contain aldehyde groups.

Particularly preferred conjugates according to the invention are characterized in that the substances that accumulate in diseased tissue are peptides such as endothelines, partial endotheline sequences, endotheline analogues, endotheline derivatives, or endotheline antagonists.

Other preferred embodiments of the conjugates according to the invention are characterized in that the peptides comprise the following sequences or parts thereof:

(SEQ ID NO: 1)
cys-ser-cys-ser-ser-leu-met-asp-lys-glu-cys-val-tyr-phe-cys-his-leu-asp-ile-ile-trp, (SEQ ID NO: 2)
cys-ser-cys-ser-ser-trp-leu-asp-lys-glu-cys-val-tyr-phe-cys-his-leu-asp-ile-ile-trp, (SEQ ID NO: 3)
cys-thr-cys-phe-thr-tyr-lys-asp-lys-glu-cys-val-tyr-tyr-cys-his-leu-asp-ile-ile-trp, (SEQ ID NO: 4)
cys-ser-ala-ser-ser-leu-met-asp-lys-glu-ala-val-tyr-phe-cys-his-leu-asp-ile-ile-trp, (SEQ ID NO: 5)
cys-ser-cys-asn-ser-trp-leu-asp-lys-glu-cys-val-tyr-phe-cys-his-leu-asp-ile-ile-trp,

```
                                                              (SEQ ID NO: 6)
   ┌─────────────────────────────┐
cys-ser-cys-lys-asp-met-thr-asp-lys-glu-cys-val-tyr-
        └──────────────────────────────────┘
phe-cys-his-gln-asp-val-ile-trp,
                                                              (SEQ ID NO: 7)
   ┌─────────────────────────────┐
ala-ser-cys-ser-ser-leu-met-asp-lys-glu-cys-val-tyr-
phe-ala-his-leu-asp-ile-ile-trp,
                                                              (SEQ ID NO: 8)
ala-ser-ala-ser-ser-leu-met-asp-lys-glu-ala-val-tyr-
phe-ala-his-leu-asp-ile-ile-trp,
                                                              (SEQ ID NO: 9)
cys-ser-cys-ser-ser-trp-leu-asp-lys-glu-ala-val-tyr-
phe-ala-his-leu-asp-ile-ile-trp,
                                                              (SEQ ID NO: 10)
┌─────────────────┐
cys-val-tyr-phe-cys-his-leu-asp-ile-ile-trp,
                                                              (SEQ ID NO: 11)
N-acetyl-leu-met-asp-lys-glu-ala-val-tyr-phe-ala-his-leu-
asp-ile-ile-trp,
the partial sequence
                                                              (SEQ ID NO: 12)
his-leu-asp-ile-ile-trp
or the cyclic amino acid sequences
                                                              (SEQ ID NO: 13)
Cyclo-(Dtrp-Dasp-pro-Dval-leu),
                                                              (SEQ ID NO: 14)
Cyclo-(Dglu-ala-alloDile-leu-Dtrp).
```

The compounds according to the invention of the general formula (I) are produced by reacting technetium-99m in the form of pertechnetate or Re in the form of perrhenate in the presence of a reductant and, optionally, an auxiliary ligand, with a compound of the general formula (II)

$$B\text{—}CO\text{—}CR^1R^2\text{—}A\text{—}CR^3R^4\text{—}CO\text{—}D \qquad (II)$$

wherein $R^1$, $R^2$, $R^3$, $R^4$, A, B, and D have the meanings specified above.

The ligands according to the invention of the general formula (II) are produced by reacting compounds of the general formula (III)

$$X\text{—}CO\text{—}CR^1R^2\text{—}A\text{—}CR^3R^4\text{—}CO\text{—}X' \qquad (III)$$

wherein $R^1$, $R^2$, $R^3$, $R^4$, and A have the meanings specified above, and X, X' represent a leaving group, with compounds of the general formula (IV)

$$H\text{—}B \qquad (IV)$$

and/or the general formula (V)

$$H\text{—}D \qquad (V)$$

where B and D have the meanings specified above.

These reactions are carried out in polar and non-polar aprotic solvents such as dichloromethane, tetrahydrofurane, chloroform, 1,4-dioxane, DMF, or DMSO at temperatures between −30 and +100° C.; an auxiliary base is added to trap any acids that may be liberated. Among these bases could be, for example: tertiary amines, alkali and alkaline-earth hydroxides, alkali and alkaline-earth carbonates.

Another object of the present invention are kits for producing radiopharmaceuticals consisting of a compound of the general formula (II) or a conjugate according to the invention containing compounds of the general formulae (I and/or II) and substances that accumulate selectively in tissues, a reductant and, optionally, an auxiliary ligand, said agents being either dry or in solution, instructions for use including instructions for reacting the compounds described with technetium-99m or rhenium in the form of a pertechnetate or perrhenate solution.

Another object of this invention is a radiopharmaceutical formulation for non-invasive in-vivo visualization of receptors and tissue containing receptors and/or atherosclerotic plaques. It contains a compound of the general formula (I) or a conjugate according to the invention containing compounds of the general formulae (I and/or II) and substances that accumulate selectively in tissues, optionally with the adjuvants common in galenics; the compound is prepared in a kit using technetium-99m or rhenium in the form of a pertechnetate or perrhenate solution.

Yet another object of this invention is a method for carrying out radiodiagnostic examinations according to which the radiopharmaceutical formulation is applied at doses from 0.1 to 30 mCi, preferably from 0.5 to 10 mCi, per 70 kg of a patient's body weight, and that radiation emitted by the patient is recorded.

Many of the synthesized chelates that were labelled with Tc-99m or Re surprisingly showed a greater stability than comparable $N_2S_2$ and $N_3S$ systems described in the literature. For example, no decomposition products were found of a substance according to the invention (Example 3a) coupled with a fatty alcohol even after 24 hours. It was also found in competition tests that the Tc-99m or Re chelating agents complex better than comparable $N_2S_2$, N3S and propylene aminoxium systems. The chelates and chelating agents described in the present invention are clearly better suited for diagnostic and therapeutic purposes than the systems known so far. It is a specific advantage of the chelating agents according to the invention that they may be synthesized without sulfur protecting groups. This makes synthesis very simple; in addition, the compounds according to the invention, when radiolabelled, do not contain any other foreign molecules in the solutions used for radiodiagnostics or radiotherapy, for example, solutions to be administered intravenously. Biodistribution of the radiopharmaceutical and thus the value of diagnostic information are frequently diminished by such foreign molecules. Moreover, such ligands or their coupling products with substances that accumulate selectively in diseased tissues can be labelled very gently. The ligands according to the invention and their coupling products with substances that accumulate selectively in diseased tissues can be labelled at room temperature and at the physiological pH value without having to split off protecting groups using bases, acids, or other auxiliary substances known to a person skilled in the art. This guarantees that the very sensitive substances that accumulate selectively in diseased tissues are not modified chemically by such auxiliary substances, as such modification frequently reduces selective accumulation in diseased tissue and diminishes the.. value of radiodiagnostic information.

Sulfur protecting groups may be used here, of course, if the disadvantages described can be accepted. The groups are attached to sulfur atoms and split off according to methods known to a person skilled in the art. The ways in which the substances that accumulate selectively in diseased tissues are bonded are also known to a person skilled in the art (e.g. Fritzberg et al.; J. Nucl. Med. 26, 7 (1987)), for example, by a reaction of electrophilic groups of the complex ligand with nucleophilic centres of the substances that accumulate selectively in diseased tissues. Otherwise, nucleophilic groups of the chelating agent are coupled with electrophilic groups of the substances that accumulate selectively in diseased tissues.

The partners for coupling are, among others, various bio-molecules, ligands that bond to specific receptors which are capable of detecting tissue showing a modified receptor density. This includes peptides, steroid hormones, growth factors, and neurotransmitters. Ways for improved diagnosis of carcinomas of the breast and the prostata were shown using ligands for steroid hormone receptors (S. J. Brandes and J. A. Katzenellenbogen, Nucl. Med. Biol. 15, 53, 1988). Tumour cells sometimes show a modified density of receptors for peptide hormones or growth factors such as the epidermal growth factor (EGF). The differences in concentration could be utilized for selective accumulation of cytostatic agents in tumour cells (E. Aboud-Pirak et al., Proc. Natl. Acad. Sci. USA 86; 3778, 1989). Ligands for neuroreceptors labelled with positron-emitting isotopes were successfully used for the diagnosis of various brain diseases (J. J. Forst, Trends in Pharmacol. Sci., 7, 490, 1989). Other bio-molecules are metabolites that can be introduced into the metabolism of cells to make changes visible; this includes fatty acids, saccharides, peptides, and amino acids. Fatty acids that were coupled with the more unstable $N_2S_2$ chelating agents have been described in EPA 0 200 492. Other metabolic products such as saccharides (desoxyglucose), lactate, pyruvate, and amino acids (leucine, methylmethionine, glycine) were used in the PET technique for visualizing changes in metabolic processes (R. Weinreich, Swiss Med., 8, 10, 1986). Likewise, non-biological substances such as misonidazol and its derivatives which bond irreversibly to cell components in tissues or parts of tissues with a reduced oxygen concentration, can be used for specific accumulation of radioactive isotopes and thus for the visualization of tumours or ischaemic regions (M. E. Shelton, J. Nucl. Med. 30; 351, 1989). Finally, bifunctional chelating agents may be coupled with monoclonal antibodies or their fragments. Coupling products of the chelating agents according to the invention or their technetium-99m or Re complexes with fatty alcohols, fatty alcohol derivatives, or fatty amines and their derivatives, or with endothelines, partial endotheline sequences, endotheline analogues, endotheline derivatives, or endotheline antagonists have proved particularly favourable for the detection of atherosclerotic vascular diseases. These derivatives were applied to WHHL rabbits that had high LDL concentrations in their blood—and thus atherosclerotic lesions—due to a genetic defect of their LDL receptor. Concentration quotients from 3 to 40 were found in atheromatose plaques as compared with undamaged tissue about 4 to 5 hours after i.v. application of the derivatives to WHHL rabbits. This allowed detection of atherosclerotic areas of vessels using the common methods of radiodiagnostics (e.g. a gamma scintillation camera). Only very late stages of atherogenesis could up to now be diagnosed by using more invasive methods (e.g. arteriography). The substances according to the invention provide the decisive advantage of being able to diagnose much earlier stages of atherosclerosis using non-invasive methods.

It is unimportant whether the chelating agent is labelled with Tc-99m or Re before or after coupling with the selectively accumulating molecule. But if coupling takes place after complexing, it is a prerequisite that the reaction of the radioactive complex with the accumulating compound is rapid, gentle, and nearly quantitative, requiring no subsequent purification.

The radiopharmaceuticals of the invention are produced in a generally known way by dissolving the complexing agents according to the invention in an aqueous medium and adding a reductant, preferably tin(II) salts such as chloride or tartrate, optionally adding the adjuvants common in galenics, and subsequent sterile filtration. Among the suitable additives are physiologically tolerable buffers (such as tromethamine), small quantities of electrolytes (e.g. sodium chloride) or stabilizers (e.g. gluconate, phosphate, or phosphonate). The pharmaceutical according to the invention is either available as a solution or as lyophilizate and is mixed shortly before application with a solution of Tc-99m pertechnetate, eluated from commercial generators, or a perrhenate solution.

For in-vivo applications in nuclear medicine, the agents according to the-invention are administered at doses from $1\times10^{-5}$ to $5\times10^{4}$ nmol/kg of body weight, preferably from $1\times10^{-3}$ to $5\times10^{2}$ nmol/kg of body weight. The amount of radioactivity per application, based on an average body weight of 70 kg, is between 0.05 and 50 mCi, preferably between 5 and 30 mCi, for diagnostic applications. For therapeutic applications, doses applied are between 5 and 500 mCi, preferably from 10 to 350 mCi. Normally, 0.1 to 2 ml of a solution of the agents according to the invention is applied by intravenous, intra-arterial, peritoneal or intra-tumoral injection. The intravenous injection is preferred.

The following examples shall explain the object of this invention in greater detail.

EXAMPLE 1a

N,N'-bis-(2-mercapto-1-(methoxycarbonyl)-ethyl)-thiodiglycolic Acid Diamide 9.35 g (0.05 mol) of thiodiglycolic acid dichloride dissolved in 250 ml of anhydrous dichloromethane are added by dropping, at 0° C. and in an argon atmosphere, to a solution of 17.16 g (0.1 mol) of cysteine methyl ester hydrochloride and 20.24 g (0.2 mol) of triethyl amine in 1 liter of anhydrous dichloromethane. This mixture is stirred for 1 hour at 0° C. and for 16 hours at room temperature. It is washed three times for reprocessing with each of the following: 2% citric acid, a saturated solution of sodium hydrogencarbonate, and water. After drying above sodium sulfate, the product is gained by evaporating the solvent under reduced pressure. It is recrystallized from diethyl ether for purification.

Yield: 15.32 g (79.7%), white powder

Analysis:

| Calc.: | C 37.49 | H 5.24 | N 7.29 | O 24.97 | S 25.02 |
|---|---|---|---|---|---|
| Found: | C 37.28 | H 5.41 | N 7.17 | | S 24.89 |

EXAMPLE 1b

Technetium-99m complex of N,N'-bis-(2-mercapto-1-(methoxycarbonyl)-ethyl)-thiodiglycolic Acid Diamide 10 mg of the ligand produced according to Example 1a are dissolved in 1.0 ml of 25% EtOH. 50 µl of this ligand solution are mixed with 250 µl of phosphate buffer, pH 9.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125×4.6 mm; gradient elution from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >98%.

EXAMPLE 2a

N,N'-bis-(2-mercapto-1-(hydroxycarbonyl)-ethyl)-thiodiglycolic Acid Diamide 3.84 g (10 mmol) of the ligand produced according to Example 1a are dissolved in 200 ml of 2N sodium hydroxide solution in an argon atmosphere. After 1.5 hours of stirring at room temperature, the solution is set to pH=2 using argon-saturated concentrated hydrochloric acid; the sedimented oil is extracted with acetic ester. After drying above sodium sulfate, the solvent is evaporated under reduced pressure. The oily crude product is crystallized by trituration with diethyl ether.

Yield: 932 mg (26.15%), white powder

Analysis:

| Calc.: | C 33.70 | H 4.52 | N 7.86 | O 26.93 | S 26.98 |
|---|---|---|---|---|---|
| Found: | C 33.49 | H 4.73 | N 7.71 | | S 26.73 |

EXAMPLE 2b

Technetium-99m complex of N,N'-bis-(2-mercapto-1-(hydroxycarbonyl)-ethyl)-thiodiglycolic Acid Diamide 10 mg of the ligand produced according to Example 2a are dissolved in 1.0 ml of 0.5 M phosphate buffer, pH 7.5. 50 µl of this ligand solution are mixed with 250 µl of phosphate buffer, pH 7.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125×4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >98%.

EXAMPLE 3a

N,N'-bis-(2-mercapto-1-(decyloxycarbonyl)-ethyl)-thiodiglycolic Acid Diamide 0.935 g (5 mmol) of thiodiglycolic acid dichloride dissolved in 50 ml of anhydrous dichloromethane are added by dropping, at 0° C. and in an argon atmosphere, to a solution of 2.98 g (10 mmol) of cysteine decyl ester hydrochloride (CA 57, 15235d) and 2.02 g (20 mmol) of triethyl amine in 250 ml of anhydrous dichloromethane. This mixture is stirred for 1 hour at 0° C. and for 16 hours at room temperature. It is washed three times for reprocessing with each of the following: 2% citric acid, a saturated solution of sodium hydrogencarbonate, and water. After drying above sodium sulfate, the product is gained by evaporating the solvent under reduced pressure. It is recrystallized from diethyl ether for purification.

Yield: 2.57 g (80.7%), white powder

Analysis:

| Calc.: | C 56.57 | H 8.86 | N 4.40 | O 15.07 | S 15.10 |
|---|---|---|---|---|---|
| Found: | C 56.43 | H 8.92 | N 4.41 | | S 14.92 |

There is the following alternative way of producing N,N'-bis- (2-mercapto-1- (decyloxycarbonyl) -ethylthiodiglycolic Acid Diamide: 190 mg (1 mmol) of p-tolenesulfonyl hydrate are added to 3.84 g (10 mmol) of the ligand described in Example 1a in 200 ml of 1-decanol, and the mixture is heated for 5 hours in an argon atmosphere to 100° C. while the methanol that forms is distilled off. When the reaction is finished, as much surplus 1-decanol as possible is distilled off in a medium high vacuum; the residue is taken up in dichloromethane. The dichloromethane solution is washed three times for reprocessing with each of the following: 2% citric acid, a saturated solution of sodium hydrogencarbonate, and water. After drying above sodium sulfate, the solvent is evaporated under reduced pressure, and the residue is chromatographed on silica gel (eluent: dichloromethane/methanol 99:1). The product is eventually recrystallized from diethyl ether.

Yield: 843 mg (13.23%), white powder

EXAMPLE 3b

Technetium 99-m complex of N,N'-bis-(2-mercapto-1-(decyloxycarbonyl)-ethyl)-thiodiglycolic Acid Diamide 10 mg of the ligand produced according to Example 3a are dissolved in 1.0 ml of ethanol. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125× 4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >95%.

EXAMPLE 4a

N,N'-bis-(2-mercapto-1-(butylamino carbonyl)-ethyl)-thiodiglycolic Acid Diamide 3.84 g (10 mmol) of the ligand produced according to Example 1a mixed with 30 ml of ethanol and 70 ml of n-butylamine are heated to boiling in an argon atmosphere for 6 h. The mixture is evaporated in a vacuum, and the residue is mixed in an argon atmosphere with 200 ml of 2% citric acid and 200 ml of dichloromethane. The mixture is strongly agitated for 15 minutes, the dichloromethane phase is separated and washed three times with each of the following: 2% citric acid, a saturated solution of sodium hydrogencarbonate, and water. After drying above sodium sulfate, the solvent is evaporated under reduced pressure. The residue is chromatographed on silica gel (eluent: dichloromethane/ methanol 95:5). Finally, the reaction mixture is recrystallized from diethyl ether.

Yield: 1.03 g (22.1%), white powder

Analysis:

| Calc.: | C 46.53 | H 6.94 | N 12.06 | O 13.77 | S 20.07 |
|---|---|---|---|---|---|
| Found: | C 46.37 | H 6.82 | N 11.89 | | S 19.78 |

EXAMPLE 4b

Technetium-99m complex of N,N'-bis-(2-mercapto-1-(butylamino carbonyl)-ethyl)-thiodiglycolic Acid Diamide 10 mg of the ligand produced according to Example 4a are dissolved in 1.0 ml of ethanol. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125× 4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >95%.

EXAMPLE 5a

N,N'-bis- (2-mercapto-1-(2-methoxyethoxy carbonyl)-ethyl)-thiodiglycolic Acid Diamide 3.84 g (10 mmol) of the ligand described in Example 1a are refluxed in an argon atmosphere for 6 hours in 250 ml of anhydrous ethylene glycol monomethyl ether in the presence of 190 mg (1 mmol) of p-toluenesulfonyl hydrate. Then the solvent is evaporated under reduced pressure and the oily residue is taken up in dichloromethane. The dichloromethane solution is washed three times with each of the following: 2% citric acid, a saturated solution of sodium hydrogen-carbonate, and water. After drying above sodium sulfate, the solvent is evaporated under reduced pressure. The oily residue obtained is chromatographed on silica gel (eluent: dichloromethane/methanol 8:2). Finally, it is recrystallized from diethyl ether.

Yield: 753 mg (15.9%), white powder

Analysis:

| Calc.: | C 40.66 | H 5.97 | N 5.93 | O 27.08 | S 20.35 |
|---|---|---|---|---|---|
| Found: | C 40.37 | H 6.08 | N 5.71 | | S 20.08 |

EXAMPLE 5b

Technetium-99m complex of N,N'-bis-(2-mercapto-1-(2-methoxyethoxy carbonyl)-ethyl)-thiodiglycolic Acid Diamide 10 mg of the ligand produced according to Example 5a are dissolved in 1.0 ml of ethanol. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125× 4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >95%.

EXAMPLE 6a

N,N'-bis-(2-mercapto-1-(2,3-dihydroxypropyl-aminocarbonyl)-ethyl)-thiodiglycolic Acid Diamide 3.84 g (10 mmol) of the ligand produced according to Example 1a are dissolved in 30 ml of ethanol and 30 ml of aminopropandiol and heated to boiling for 7 hours in an argon atmosphere. The ethanol is distilled off under reduced pressure, and the residue is mixed with argon-saturated water; a pH value=7 is set using argon-saturated concentrated hydrochloric acid. The yellowish solution is lyophilized and the residue chromatographed on silica gel RP 18 (eluent: water, tetrahydrofurane 0–50%). A colourless glass is obtained after evaporating the solvent.

Yield: 513 mg (10.2%), colourless glass

Analysis referring to the anhydrous substance:

| Calc.: | C 38.23 | H 6.02 | N 11.15 | O 25.47 | S 19.14 |
|---|---|---|---|---|---|
| Found: | C 38.11 | H 6.28 | N 10.88 | | S 18.95 |

Example 6b

Technetium-99m complex of N,N'-bis-(2-mercapto-1-(2,3-dihydroxypropyl-aminocarbonyl)-ethyl)-thiodiglycolic Acid Diamide 10 mg of the ligand produced according to Example 6a are dissolved in 1.0 ml of 50% ethanol. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125× 4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >95%.

EXAMPLE 7a

N-(4-thia-1-(ethoxy-carbonyl)-pentyl)-thiodiglycolic Acid Monoamide 13.21 g (0.1 mol) of thiodiglycolic acid anhydride dissolved in 500 ml of anhydrous dichloromethane are added by dropping, at 0° C. and in an argon atmosphere, to a solution of 21.37 g (0.1 mol) of methionine ethyl ester hydrochloride and 20.24 g (0.2 mol) of triethyl amine in 1 liter of anhydrous dichloromethane. This mixture is stirred for 1 hour at 0° C. and for 16 hours at room temperature. It is washed with 2% citric acid for reprocessing. A pH value=2 is set by dropping in concentrated hydrochloric acid while keeping the mixture agitated. The organic phase is separated and dried above sodium sulfate. A yellowish oil which can be used without purification for further reactions is obtained after evaporating the solvent under reduced pressure.

Yield: 25.74 g (83.2%), yellowish oil

Analysis referring to the anhydrous substance:

| Calc.: | C 42.70 | H 6.19 | N 4.53 | O 25.86 | S 20.72 |
|---|---|---|---|---|---|
| Found: | C 42.37 | H 6.62 | N 4.15 | | S 20.31 |

EXAMPLE 7b

N-(4-thia-1-(ethoxy-carbonyl)-pentyl-N'-(2-oxo-tetrahydrothiophene-3-yl)-thiodiglycolic Acid Diamide 1.09 g (10 mmol) of ethyl chloroformate dissolved in 25 ml of anhydrous dichloromethane are added by dropping, and at −15° C., to a solution of 3.09 g (10 mmol) of the thiodiglycolic acid monoamide derivative produced in Example 7a and 2.02 g (20 mmol) of triethyl amine in 100 ml of dichloromethane. When activation is finished (45 minutes), a solution of 1.54 g (10 mmol) of homocysteine thiolactone hydrochloride and 2.02 g (10 mmol) of triethyl amine in 25 ml of anhydrous dichloromethane are added by dropping. The mixture is stirred for 1 hour at −15° C. and allowed to stand overnight and warm up to room temperature. The dichloromethane solution is washed three times for reprocessing with each of the following: 2% citric acid, a saturated solution of sodium hydrogencarbonate, and water. After drying above sodium sulfate, the product is gained by evaporating the solvent under reduced pressure. The residue is recrystallized from diethyl ether.

Yield: 3.75 g (91.8%), white powder

Analysis:

| Calc.: | C 44.10 | H 5.92 | N 6.86 | O 19.58 | S 23.54 |
|---|---|---|---|---|---|
| Found: | C 43.97 | H 5.98 | N 6.72 | | S 23.31 |

EXAMPLE 7c

N-(4-thia-1-(ethoxy-carbonyl)-pentyl-N'-(3-mercapto-1-(butylaminocarbonyl)-propyl)-thiodiglycolic Acid Diamide 0.731 g (10 mmol) of butylamine are added in an argon atmosphere to a solution of 2.04 g (5 mmol) of the thiolactone derivative of the thiodiglycolic acid diamide produced in Example 7b dissolved in 20 ml of anhydrous dichloromethane. The reaction mixture is stirred at room temperature overnight and evaporated under reduced pressure. It is then intermixed with aqueous 2% citric acid and dichloromethane and stirred thoroughly. After the organic phase has been separated off, it is washed three times with each of the following: aqueous 2% citric acid, a saturated solution of sodium hydrogencarbonate, and water. After drying above sodium sulfate, the solvent is evaporated under reduced pressure. The residue may be chromatographed on silica gel for purification (eluent: dichloromethane/ methanol 95:5).

Yield: 1.51 g (62.7%), white powder

Analysis:

| Calc.: | C 47.38 | H 7.32 | N 8.72 | O 16.61 | S 19.97 |
|---|---|---|---|---|---|
| Found: | C 47.23 | H 7.41 | N 8.62 | | S 19.79 |

EXAMPLE 7d

Technetium-99m complex of N-(4-thia-1-(ethoxy-carbonyl)-pentyl-N'-(3-mercapto-1-(butyl aminocarbonyl)-propyl)-thiodiglycolic Acid Diamide 10 mg of the ligand produced according to Example 7c are dissolved in 1.0 ml of ethanol. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125×4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >95%.

EXAMPLE 8a

N-(4-thia-1-(hydroxy-carbonyl)-pentyl-N'-(3-mercapto-1-(hydroxy-carbonyl)-propyl)-thiodiglycolic Acid Diamide 2.04 g (5 mmol) of the thiolactone derivative of thiodiglycolic acid diamide produced according to Example 7b in 500 ml of aqueous sodium hydroxide solution are dissolved in an argon atmosphere in 50 ml of ethanol. The mixture is stirred for 1 hour at room temperature; a pH value=2 is set using argon-saturated concentrated hydrochloric acid. The separated oil is extracted with argon-saturated ethyl acetate. After drying the organic phase above sodium sulfate, it is evaporated under reduced pressure, and the oily crude product is crystallized from diethyl ether by trituration.

Yield: 666 mg (33.4%), white powder

Analysis referring to the anhydrous substance:

| Calc.: | C 39.18 | H 5.56 | N 7.03 | O 24.09 | S 24.13 |
|---|---|---|---|---|---|
| Found: | C 39.02 | H 5.79 | N 6.84 | | S 23.83 |

EXAMPLE 8b

Technetium-99m complex of N-(4-thia-1- (hydroxy-carbonyl)-pentyl-N'-(3-mercapto-1-(hydroxy-carbonyl)-propyl)-thiodiglycolic Acid Diamide 10 mg of the ligand produced according to Example 8a are dissolved in 1.0 ml of 0.5 M phosphate buffer, pH 7.5. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125×4.6 mm; gradient eluation from 100% A to 100% B within 7.5 minutes (eluent A: sodium hydrogenphosphate, 0.005 M, pH 7.4; eluent B: acetonitrile/sodium hydrogenphosphate, 0.005 M, pH 7.4 (75/25); 2.0 ml/min. Radiochemical purity is >95%.

EXAMPLE 9a

N-(3-mercapto-1-(carbonyl-gly-his-leu-asp-ile-ile-trp)-propyl)-N'-(4-thia-1-(ethoxy-carbonyl)-pentyl)-thiodiglycolic Acid Diamide 408.5 mg (1 mmol) of the N-(4-thia-1-(ethoxy-carbonyl)-pentyl-N'-(2-oxo-tetrahydrothiophene-3-yl) -thiodiglycolic acid diamide produced in Example 7b are added in an argon atmosphere to a solution of 853 mg (1 mmol) of $NH_2$-gly-his-leu-asp-ile-ile-trp SEQ ID NO: 5) (produced in a similar way as described by Barany and Merrifield, The Peptides: Analysis, Biology, Academic Press, New York 1980; Stewart and Young, Solid Phase Peptides Syntheses, 2nd ed., Pierce Chemical W., Rockford, II, 1984) and 304 mg (3 mmol) of triethyl amine in 100 ml of dimethyl formamide. The resulting reaction mixture is stirred at room temperature for 14 hours. When the reaction is finished, the solution is filtered and the solvent removed under reduced pressure. The residual oil is mixed three times with 50 ml of dimethyl formamide and evaporated each time. The residue is stirred up with 200 ml of anhydrous diethyl ether. A white solid material settles down which is filtered off. The material is recrystallized from mixtures of dimethyl formamide and diethyl ether for purification.

Yield: 345 mg (27.3%), white powder

Analysis referring to the anhydrous substance:

| Calc.: | C 53.32 | H 6.71 | N 13.32 | O 19.02 | S 7.62 |
|---|---|---|---|---|---|
| Found: | C 53.17 | H 6.83 | N 13.19 | | S 7.42 |

EXAMPLE 9b

Technetium-99m complex of N-(3-mercapto-1-(carbonyl-gly-his-leu-asp-ile-ile-trp)-propyl)-N'-(4-thia-1-(ethoxy-carbonyl)-pentyl)-thiodiglycolic Acid Diamide 10 mg of the ligand produced according to Example 9a are dissolved in 1.0 ml of 0.5 M phosphate buffer, pH 7.5. 50 µl of this ligand solution are mixed with 250 µl of phosphate buffer, pH.8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125×4.6 mm; gradient eluation from 100% A to 100% B within 7.5 minutes (eluent A: sodium hydrogenphosphate, 0.005 M, pH 7.4; eluent B: acetonitrile/ sodium hydrogenphosphate, 0.005 M, pH 7.4 (75/25); 2.0 ml/min. Radiochemical purity is >96%.

EXAMPLE 10a

N-(3-mercapto-1-(carbonyl-gly-his-leu-asp-ile-ile-trp)-propyl)-N'-(4-thia-1-(hydroxy-carbonyl)-pentyl)-thiodiglycolic Acid Diamide 126 mg (0.1 mmol) of the N-(3-mercapto-1-(carbonyl-gly-his-leu-asp-ile-ile-trp)-propyl)-N'-(4-thia-1-(ethoxy-carbonyl)-pentyl)-thiodiglycolic acid diamide produced in Example 9a are dissolved in an argon atmosphere in 50 ml of aqueous 0.1 N sodium hydroxide solution. The mixture is stirred for 1 hour at room temperature; a pH value=7 is set using 1 N aqueous hydrochloric acid. The crude product is isolated by lyophilization. It is chromatographed on silica gel RP 18 (eluent: water/tetrahydrofurane; tetrahydrofurane 0–30%). The fractions that contain the target compound are lyophilized after distilling off the tetrahydrofurane. The residue is dissolved in a small quantity of water, a pH value=2 is set by adding aqueous hydrochloric acid, and the product is filtered off.

Yield: 23 mg (18.6%), white powder

Analysis referring to the anhydrous substance:

| Calc.: | C 52.58 | H 6.54 | N 13.63 | O 19.46 | S 8.00 |
|---|---|---|---|---|---|
| Found: | C 52.37 | H 6.79 | N 13.41 | | S 7.77 |

EXAMPLE 10b

Technetium-99m complex of N-(3-mercapto-1-(carbonyl-gly-his-leu-asp-ile-ile-trp)-propyl)-N'-(4-thia-1-(hydroxy-carbonyl)-pentyl)-thiodiglycolic Acid Diamide 10 mg of the ligand produced according to Example 10a are dissolved in 1.0 ml of 0.5 M phosphate buffer, pH 7.5. 50 µl of this ligand solution are mixed with 250 µl of phosphate buffer, pH 8.5, 50 µl of a deoxygenated aqueous citrate solution (50 mg/ml), 2.5 µl of a deoxygenated aqueous tin(II) chloride solution (5 mg/ml 0.05 N HCl), and 100 µl of a pertechnetate solution (400–900 µCi). After an incubation time of 10 minutes, the reaction mixture is tested for purity of the Tc complex formed using HPLC: Hamilton PRP-1 column, 5 µm, 125×4.6 mm; gradient elution from 100% A to 100% B within 7.5 minutes (eluent A: sodium hydrogenphosphate, 0.005 M, pH 7.4;eluent B: acetonitrile/ sodium hydrogenphosphate, 0.005 M, pH 7.4 (75/25); 2.0 ml/min. Radiochemical purity is >95%.

EXAMPLE 11

Accumulation of N,N'-bis-(2-mercapto-1-(decyloxycarbonyl)-ethyl)-thiodiglycolic Acid Diamide, technetium-99m Complex, in Atherosclerotic Vascular Lesions of WHHL Rabbits N,N'-bis-(2-mercapto-1-(decyloxycarbonyl)-ethyl-thiodiglycolic acid diamide (produced according to Example 3a) is labelled as described in Example 3b.

99.9 GBq (2.7 mCi) of the substance labelled according to Example 3b were diluted to 1 ml with phosphor-buffered saline and administered via the ear vein to a narcotized WHHL rabbit, Rompun/Ketavet (1:2). The rabbit was killed 5 hours after the application, and an autoradiogram of the aorta as well as a Sudan(III) staining were carried out to visualize the atherosclerotic plaques (FIG. 1). The accumulation factor between normal and atherosclerotic walls was between 3 and 8 depending on the thickness of the plaques (Sudan(III) staining).

---

What is claimed is:

1. A compound of the general formula (I)

  (I)

wherein M represents a radionuclide of Tc or Re, and L represents a ligand of the general formula (II)

$$B—CO—CR^1R^2—A—CR^3R^4—CO—D \quad (II)$$

wherein

A is selected from the group consisting of an O chalcogen atom, an S chalcogen atom, and an Se chalcogen atom, $R^2$, $R^3$, and $R^4$ are the same or different and are selected from the group consisting of a hydrogen atom, and a branched or unbranched $C_1$–$C_6$ alkyl group, B and D are the same or different and represent a residue

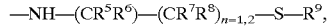

wherein $R^5$ and $R^6$ are the same or different and are selected from the group consisting of a hydrogen atom and an unbranched, branched, cyclic, or polycyclic $C_1$–$C_{60}$ alkyl, alkenyl, polyalkenyl, alkynyl, polyalkynyl, aryl, alkylaryl, or arylalkyl group which optionally carry additional hydroxy, carboxy, aminocarbonyl, alkoxycarbqnyl, amino, aldehyde, oxo, oxy, or alkoxy groups containing up to 20 carbon atoms, optionally interrupted, and replaced, by one or several heteroatoms selected from the group consisting of O, N, S, P, As, and Se, $R^7$ and $R^8$ are the same or different and are selected from the group consisting of a hydrogen atom and a branched or unbranched $C_1$–$C_6$ alkyl group, $R^9$ is selected from the group consisting of a hydrogen atom, a branched or unbranched $C_1$–$C_6$ alkyl group, and a sulfur protecting group, with $R^9$ and $R^5$, together with the groups that connect them, optionally forming a 4- to 8-membered ring which optionally carry additional hydroxy, oxo, oxy, or alkoxy groups containing up to 6 carbon atoms.

2. A method for the production of compounds of the general formula (I)

$$M\text{—}L \qquad (I)$$

comprising reacting technetium-99m or Re in the form of pertechnetate or perrhenate in the presence of a reductant and, optionally, an auxiliary ligand, with a compound of the general formula (II)

$$B\text{—}CO\text{—}CR^1R^2\text{—}A\text{—}CR^3R^4\text{—}CO\text{—}D \qquad (II)$$

wherein $R^1$, $R^2$, $R^3$, $R^4$, A, B, and D have the meanings specified in claim 1.

3. A method for the production of ligands of the general formula (II)

$$B\text{—}CO\text{—}CR^1R^2\text{—}A\text{—}CR^3R^4\text{—}CO\text{—}D \qquad (II)$$

comprising reacting compounds of the general formula (III)

$$X\text{—}CO\text{—}CR^1R^2\text{—}A\text{—}CR^3R^4\text{—}CO\text{—}X' \qquad (III)$$

wherein $R^1$, $R^2$, $R^3$, $R^4$, and A have the meanings specified in claim 1, and X, X' represent a leaving group, with compounds of the general formula (IV)

$$H\text{—}B \qquad (IV)$$

and/or a reactant of the general formula (V)

$$H\text{—}D \qquad (V)$$

wherein B and D are as specified in claim 1.

4. A conjugate of a compound, the conjugate containing a substance that accumulates selectively in diseased tissues, with a covalent bond existing between the compound and the substance, said bond being amidic if the substance contains a carboxy or an amino group, ester-like if the substance contains a hydroxy group, and imidic if the substance contains aldehyde groups, the compound having the general formula (II)

$$B\text{—}CO\text{—}CR^1R^2\text{—}A\text{—}CR^3R^4CO\text{—}D \qquad (II)$$

wherein

A is selected from the group consisting of an O chalcogen atom, an S chalcogen atom, and an Se chalcogen atom, $R^1$, $R^2$, $R^3$, and $R^4$ are the same or different and are selected from the group consisting of a hydrogen atom, and a branched or unbranched $C_1$–$C_6$ alkyl group, B and D are the same or different and represent a residue $$-\text{NH}-(CR^5R^5)-(CR^7R^8)_{n=1,2}-S-R^9,$$

wherein $R^5$ and $R^6$ are the same or different and are selected from the group consisting of a hydrogen atom and an unbranched, branched, cyclic, or polycyclic $C_1$–$C_{60}$ alkyl, alkenyl, polyalkenyt, alkynyl, polyalkynyl, aryl, alkylaryl, or arylalkyl group which optionally carry one or more additional hydroxy, carboxy, aminocarbonyl, alkoxycarbonyl, amino, aldehyde, oxo, oxy, or alkoxy groups containing up to 20 carbon atoms, optionally interrupted or replaced, by one or several heteroatoms selected from the group consisting of O, N, S, P, As, and Se, $R^7$ and $R^8$ are the same or different and are selected from the group consisting of a hydrogen atom, and a branched or unbranched $C_1$–$C_6$ alkyl group, $R^9$ is selected from the group consisting of a hydrogen atom, a branched or unbranched $C_1$–$C_6$ alkyl group, and a sulfur protecting group, with $R^9$ and $R^5$, together with the groups that connect them, optionally forming a 4- to 8-membered ring which optionally carry one or more additional hydroxy, oxo, oxy, or alkoxy groups containing up to 6 carbon atoms, and a complex thereof with radioisotopes of Tc or Re.

5. A kit for producing radiopharmaceuticals consisting of a conjugate according to claim 4, a reductant and, optionally, an auxiliary ligand, said conjugate, reductant and auxiliary ligand being either dry or in solution, instructions for use including instructions for reacting the compounds with technetium-99m or rhenium in the form of a pertechnetate or perrhenate solution.

6. A radiopharmaceutical formulation for non-invasive invivo visualization of receptors and tissue containing receptors and/or atherosclerotic plaques characterized in that it contains a conjugate according to claim 4, and, optionally, the adjuvants common in galenics, and in that the compound is prepared in a kit using technetium-99m or rhenium in the form of a pertechnetate or perrhenate solution.

7. A method for carrying out radiodiagnostic examinations comprising applying a radiopharmaceutical formulation according to claim 6 at doses from 0.1 to 30 mCi per 70 kg of a patient's body weight; and recording radiation emitted by the patient.

8. A compound of the general formula (II)

$$B\text{—}CO\text{—}CR^1R^2\text{—}A\text{—}CR^3R^4\text{—}CO\text{—}D \qquad (II)$$

wherein

A is selected from the group consisting of an O chalcogen atom, an S chalcogen atom, and an Se chalcogen atom, $R^1$, $R^2$, $R^3$, and $R^4$ are the same or different and are selected from the group consisting of a hydrogen atom, and a branched or unbranched $C_1$–$C_6$ alkyl group, B and D are the same or different and represent a residue $$-\text{NH}-(CR^6R^6)-(CR^7R^8)_{n=1,2}-S-R^9,$$

wherein $R^5$ and $R^6$ are the same or different and are selected from the group consisting of a hydrogen atom and an unbranched, branched, cyclic, or polycyclic $C_1$–$C_{60}$ alkyl, alkenyt, polyalkenyl, alkynyl, polyalkynyl, aryl, alkylaryt, or arylalkyl residue which optionally carry one or more additional hydroxy, carboxy, aminocarbonyl, alkoxycarbonyl, amino, aldehyde, oxo, oxy, or alkoxy groups containing up to 20 carbon atoms, optionally interrupted or replaced by one or several heteroatoms selected from the group consisting of O, N, S, P, As, and Se, $R^7$ and $R^8$ are the same or different and are selected from the group consisting of a hydrogen atom, and a branched or unbranched $C_1$–$C_6$ alkyl group, $R^9$ is selected from the group consisting of a hydrogen atom, a branched or unbranched $C_1$–$C_6$ alkyl group, and a sulfur protecting group, with $R^9$ and $R^5$, together with the groups that connect them, optionally forming a 4- to 8-membered ring which optionally carry one or more additional hydroxy, oxo, oxy, or alkoxy groups containing up to 6 carbon atoms, and a complex thereof with radioisotopes of Tc or Re.

9. A compound according to claim 8, characterized in that $R^1$, $R^2$, $R^3$, $R^4$, and $R^5$ are hydrogen atoms.

10. A radiopharmaceutical formulation for non-invasive in-vivo visualization of receptors and tissue containing receptors and/or atherosclerotic plaques characterized in that it contains a compound according to claim 9, and, optionally, adjuvants common in galenics.

11. A compound according to claim 8, characterized in that $R^1$, $R^2$, $R^3$, $R^4$, $R^5$, $R^7$ and $R^8$ are hydrogen atoms.

12. A radiopharmaceutical formulation for non-invasive in-vivo visualization of receptors and tissue containing receptors and/or atherosclerotic plaques characterized in that it contains a compound according to claim 11, and, optionally, adjuvants common in galenics.

13. A radiopharmaceutical formulation for non-invasive in-vivo visualization of receptors and tissue containing receptors and/or atherosclerotic plaques characterized in that it contains a compound according to claim 8, and, optionally, adjuvants common in galenics.

14. A method for the production of the compound of claim 8 of the general formula (II)

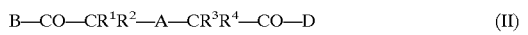
$$B\text{—}CO\text{—}CR^1R^2\text{—}A\text{—}CR^3R^4\text{—}CO\text{—}D \qquad (II)$$

comprising reacting a first reactant of the general formula (III)

$$X\text{—}CO\text{—}CR^1R^2\text{—}A\text{—}CR^3R^4\text{—}CO\text{—}X' \qquad (III)$$

wherein $R^1$, $R^2$, $R^3$, $R^4$, and A have the meanings specified in claim 8, and X, X' represent a leaving group, with a second reactant of the general formula (IV)

$$H\text{—}B \qquad (IV)$$

and/or a reactant of the general formula (V)

$$H\text{—}D \qquad (V)$$

wherein B and D are the same or different and represent a residue

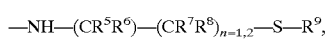
$$\text{—}NH\text{—}(CR^5R^6)\text{—}(CR^7R^8)_{n=1,2}\text{—}S\text{—}R^9,$$

wherein $R^5$ and $R^6$ are the same or different and are selected from the group consisting of a hydrogen atom and an unbranched, branched, cyclic, or polycyclic $C_1$–$C_{60}$ alkyl, alkenyl, polyalkenyl, alkynyl, polvalkynyl, aryl, alkylaryl, or arylalkyl group which optionally carry additional hydroxy, carboxy, aminocarbonyl, alkoxycarbonyl, amino, aldehyde, oxo, oxy, or alkoxy groups containing up to 20 carbon atoms. optionally interrupted, and replaced, by one or several heteroatoms selected from the group consisting of O, N, S, P, As, and Se, $R^7$ and $R^8$ are the same or different and are selected from the group consisting of a hydrogen atom and a branched or unbranched $C_1$–$C_6$ alkyl group, $R^9$ is selected from the group consisting of a hydrogen atom a branched or unbranched $C_1$–$C_6$ alkyl group and a sulfur protecting group, with $R^9$ and $R^5$, together with the groups that connect them, optionally forming a 4- to 8-membered ring which optionally carry additional hydroxy, oxo, oxy, or alkoxy groups containing up to 6 carbon atoms and that optionally the compound prepared in this way is conjugated with a substance that accumulates in diseased tissue or tumors to form a conjugate, with a covalent bond existing between the compound and the substance, said bond being amidic if the substance contains carboxy or amino groups, ester-like if the substance contains a hydroxy group, and imidic if the substance contains aldehyde groups, and that the compound or conjugate prepared in this way is reacted with technetium 99m or Re in the form of pertechnetate or perrhenate in the presence of a reductant and, optionally, auxiliary ligand.

15. A method for the production of the conjugate of claim 4 which includes a compound of the general formula (II)

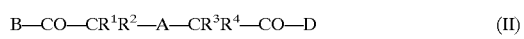
$$B\text{—}CO\text{—}CR^1R^2\text{—}A\text{—}CR^3R^4\text{—}CO\text{—}D \qquad (II)$$

comprising reacting a first reactant of the general formula (III)

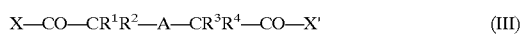
$$X\text{—}CO\text{—}CR^1R^2\text{—}A\text{—}CR^3R^4\text{—}CO\text{—}X' \qquad (III)$$

wherein $R^1$, $R^2$, $R^3$, $R^4$, and A have the meanings specified in claim 4, and X, X' represent a leaving group, with a second reactant of the general (IV)

$$H\text{—}B \qquad (IV)$$

and/or a reactant of the general formula (V)

$$H\text{—}D \qquad (V)$$

wherein B and D have the meanings specified in claim 4 and that the compound prepared in this way is conjugated with a substance that accumulates in diseased tissue or tumors to form a conjugate, with a covalent bond existing between the compound and the substance, said bond being amidic if the substance contains carboxy or amino groups, ester-like if the substance contains a hydroxy group, and imidic if the substance contains aldehyde groups, and that the conjugate prepared in this way is reacted with technetium 99m or Re in the form of pertechnetate or perrhenate in the presence of a reductant and, optionally, auxiliary ligand.

16. A compound according to claim 1, characterized in that $R^1$, $R^2$, $R^3$, $R^4$ and $R^5$ are hydrogen atoms.

17. A conjugate of a compound according to claim 4, characterized in that the substance that accumulates in diseased tissue is a peptide and is selected from the group consisting of an endotheline, a partial endotheline sequence, and an endotheline antagonist.

18. A conjugate of a compound according to claim 17, characterized in that the peptide is selected from the group consisting of:

19. A radiopharmaceutical formulation for non-invasive in-vivo visualization of receptors and tissue containing receptors and/or atherosclerotic plaques characterized in that it contains a conjugate according to claim 18 and, optionally, adjuvants common in galenics.

20. A conjugate of a compound of general formula (I) according to claimed the compound of general formula (I) having a covalent bond with a second compound, the covalent bond is amidic, ester-like, or imidic if the compound of general formula (I) is bonded to an amino, an hydroxyl or an aldehyde group of the second compound, respectively.

21. The conjugate according to claim 20, wherein the second compound is an amino acid sequence.

22. The conjugate according to claim 21 wherein the amino acid sequence is selected from the group consisting of:

(SEQ ID NO: 1)
cys-ser-cys-ser-ser-leu-met-asp-lys-glu-cys-val-tyr-phe-cys-his-leu-asp-ile-ile-trp, (SEQ ID NO: 2)
cys-ser-cys-ser-ser-trp-leu-asp-lys-glu-cys-val-tyr-phe-cys-his-leu-asp-ile-ile-trp, (SEQ ID NO: 3)
cys-thr-cys-phe-thr-tyr-lys-asp-lys-glu-cys-val-tyr-tyr-cys-his-leu-asp-ile-ile-trp, (SEQ ID NO: 4)
cys-ser-ala-ser-ser-leu-met-asp-lys-glu-ala-val-tyr-phe-cys-his-leu-asp-ile-ile-trp, (SEQ ID NO: 5)
cys-ser-cys-asn-ser-trp-leu-asp-lys-glu-cys-val-tyr-phe-cys-his-leu-asp-ile-ile-trp, (SEQ ID NO: 6)
cys-ser-cys-lys-asp-met-thr-asp-lys-glu-cys-val-asn-phe-cys-his-gln-asp-val-ile-trp, (SEQ ID NO: 7)
ala-ser-cys-ser-ser-leu-met-asp-lys-glu-cys-val-tyr-phe-ala-his-leu-asp-ile-ile-trp, (SEQ ID NO: 8)
ala-ser-ala-ser-ser-leu-met-asp-lys-glu-ala-val-tyr-phe-ala-his-leu-asp-ile-ile-trp, (SEQ ID NO: 9)
cys-ser-cys-ser-ser-trp-leu-asp-lys-glu-ala-val-tyr-phe-ala-his-leu-asp-ile-ile-trp, (SEQ ID NO: 10)
cys-val-tyr-phe-cys-his-leu-asp-ile-ile-trp, (SEQ ID NO: 11)
N-acetyl-leu-met-asp-lys-glu-ala-val-tyr-phe-ala-his-leu-asp-ile-ile-trp, (SEQ ID NO: 12)
his-leu-asp-ile-ile-trp, (SEQ ID NO: 13)
Cyclo-(Dtrp-Dasp-pro-Dval-leu), and (SEQ ID NO: 14)
Cyclo-(Dglu-ala-alloDile-leu-Dtrp).

```
cys-ser-cys-ser-ser-leu-met-asp-lys-glu-cys-val-                    (SEQ ID NO: 1)
    |_____|                         |
tyr-phe-cys-his-leu-asp-ile-ile-trp,
        |_____|
                                                                    (SEQ ID NO: 2)
cys-ser-cys-ser-ser-trp-leu-asp-lys-glu-cys-val-
    |_____|                             |
tyr-phe-cys-his-leu-asp-ile-ile-trp,
        |_____|
                                                                    (SEQ ID NO: 3)
cys-thr-cys-phe-thr-tyr-lys-asp-lys-glu-cys-val-
    |_____|                             |
tyr-tyr-cys-his-leu-asp-ile-ile-trp,
        |_____|
                                                                    (SEQ ID NO: 4)
cys-ser-ala-ser-ser-leu-met-asp-lys-glu-ala-valtyr-phe-cys-his-leu-asp-ile-ile-trp,
        |_____|
                                                                    (SEQ ID NO: 5)
cys-ser-cys-asn-ser-trp-leu-asp-lys-glu-cys-val-
    |_____|                             |
tyr-phe-cys-his-leu-asp-ile-ile-trp,
        |_____|
                                                                    (SEQ ID NO: 6)
cys-ser-cys-lys-asp-met-thr-asp-lys-glu-cys-val-
    |_____|                             |
asn-phe-cys-his-gln-asp-val-ile-trp,
        |_____|
                                                                    (SEQ ID NO: 7)
ala-ser-cys-ser-ser-leu-met-asp-lys-glu-cys-val-
        |_____|
tyr-phe-ala-his-leu-asp-ile-ile-trp,
                                                                    (SEQ ID NO: 8)
ala-ser-ala-ser-ser-leu-met-asp-lys-glu-ala-val-
tyr-phe-ala-his-leu-asp-ile-ile-trp,
                                                                    (SEQ ID NO: 9)
cys-ser-cys-ser-ser-trp-leu-asp-lys-glu-ala-val-
tyr-phe-ala-his-leu-asp-ile-ile-trp,
                                                                    (SEQ ID NO: 10)
 _____
cys-val-tyr-phe-cys-his-leu-asp-ile-ile-trp,
                                                                    (SEQ ID NO: 11)
N-acetyl-leu-met-asp-lys-glu-ala-val-tyr-phe-ala-
his-leu-asp-ile-ile-trp,
                                                                    (SEQ ID NO: 12)
his-leu-asp-ile-ile-trp,
                                                                    (SEQ ID NO: 13)
Cyclo-(Dtrp-Dasp-pro-Dval-leu), and
                                                                    (SEQ ID NO: 14)
Cyclo-(Dglu-ala-alloDile-leu-Dtrp).
```

23. A radiopharmaceutical formulation for non-invasive in-vivo visualization of receptors and tissue containing receptors and/or atherosclerotic plaques charcterized in that it contains a conjugate according to claim 22, and, optionally, adjuvants common in galenics.

24. A radiopharmaceutical formulation for non-invasive in-vivo visualization of receptors and tissue containing receptors and/or atherosclerotic plaques characterized in that it contains a conjugate according to claim 16, and, optionally, adjuvants common in galenics.

25. A radiopharmaceutical formulation for non-invasive in-vivo visualization of receptors and tissue containing receptors and/or atherosclerotic plaques characterized in that it contains a conjugate according to claim 17, optionally, adjuvants common in galenics.

26. A conjugate according to claim 4, characterized in that $R^1$, $R^2$, $R^3$, $R^4$, $R^5$, $R^7$ and $R^8$ are hydrogen atoms.

27. A radiopharmaceutical formulation for non-invasive in-vivo visualization of receptors and tissue containing receptors and/or atherosclerotic plaques characterized in that it contains a conjugate according to claim 9, and, optionally, adjuvants common in galenics.

28. A conjugate according to claim 21, characterized in that the substance that accumulates in diseased tissue is a peptide selected from the group consisting of an endotheline, a partial endotheline sequence, and an endotheline antagonist.

29. A conjugate according to claim 28, characterized in that the peptide is selected from the group consisting of:

```
cys-ser-cys-ser-ser-leu-met-asp-lys-glu-cys-val-        (SEQ ID NO: 1)
    |_____|
tyr-phe-cys-his-leu-asp-ile-ile-trp,
    |_____| cys-ser-cys-ser-ser-trp-leu-asp-lys-glu-cys-val-        (SEQ ID NO: 2)
    |_____|
tyr-phe-cys-his-leu-asp-ile-ile-trp,
    |_____| cys-thr-cys-phe-thr-tyr-lys-asp-lys-glu-cys-val-        (SEQ ID NO: 3)
    |_____|
tyr-tyr-cys-his-leu-asp-ile-ile-trp,
    |_____| cys-ser-ala-ser-ser-leu-met-asp-lys-glu-ala-val-        (SEQ ID NO: 4)
    |
tyr-phe-cys-his-leu-asp-ile-ile-trp,
    |___| cys-ser-cys-asn-ser-trp-leu-asp-lys-glu-cys-val-        (SEQ ID NO: 5)
    |_____|
tyr-phe-cys-his-leu-asp-ile-ile-trp,
    |_____| cys-ser-cys-lys-asp-met-thr-asp-lys-glu-cys-val-        (SEQ ID NO: 6)
    |_____|
asn-phe-cys-his-gln-asp-val-ile-trp,
    |_____| ala-ser-cys-ser-ser-leu-met-asp-lys-glu-cys-val-        (SEQ ID NO: 7)
        |_____|
tyr-phe-ala-his-leu-asp-ile-ile-trp, ala-ser-ala-ser-ser-leu-met-asp-lys-glu-ala-val-        (SEQ ID NO: 8)
tyr-phe-ala-his-leu-asp-ile-ile-trp, cys-ser-cys-ser-ser-trp-leu-asp-lys-glu-ala-val-        (SEQ ID NO: 9)
tyr-phe-ala-his-leu-asp-ile-ile-trp, (SEQ ID NO: 10)
|_____|
cys-val-tyr-phe-cys-his-leu-asp-ile-ile-trp, N-acetyl-leu-met-asp-lys-glu-ala-val-tyr-phe-ala-       (SEQ ID NO: 11)
his-leu-asp-ile-ile-trp, (SEQ ID NO: 12)
his-leu-asp-ile-ile-trp, (SEQ ID NO: 13)
Cyclo-(Dtrp-Dasp-pro-Dval-leu), and (SEQ ID NO: 14)
Cyclo-(Dglu-ala-alloDile-leu-Dtrp).
```

30. A radiopharmaceutical formulation for non-invasive in-vivo visualization of receptors and tissue containing receptors and/or atherosclerotic plaques characterized in that it contains a conjugate according to claim 29, and, optionally, adjuvants common in galenics.

31. A radiopharmaceutical formulation for non-invasive in-vivo visualization of receptors and tissue containing receptors and/or atherosclerotic plaques characterized in that it contains a conjugate according to claim 29, and, optionally, adjuvants common in galenics.

32. A radiopharmaceutical formulation for non-invasive in-vivo visualization of receptors and tissue containing receptors and/or atherosclerotic plaques characterized in that it contains a conjugate according to claim 4 and, optionally, adjuvants common in galenics.

33. A radiopharmaceutical formulation for non-invasive in-vivo visualization of receptors and tissue containing receptors and/or atherosclerotic plaques characterized in that it contains a conjugate according to claim 28, and, optionally, adjuvants common in galenics.

34. A radiopharmaceutical formulation for non-invasive in-vivo visualization of receptors and tissue containing receptors and/or atherosclerotic plaques characterized in that it contains a conjugate according to claim 28, and, optionally, adjuvants common in galenics.

35. A radiopharmaceutical formulation for non-invasive in-vivo and/or atherosclerotic plaques characterized in that it contains a conjugate according to claim 34, and, optionally, adjuvants common in galenics.

36. A radiopharmaceutical formulation for non-invasive in-vivo visualization of receptors and tissue containing receptors and/or atherosclerotic plaques characterized in that it contains a conjugate according to claim 26, and, optionally, adjuvants common in galenics.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:1:

Cys Ser Cys Ser Ser Leu Met Asp Lys Glu Cys Val Tyr Phe Cys His
1               5                   10                  15

Leu Asp Ile Ile Trp
            20

(2) INFORMATION FOR SEQ ID NO:2:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

Cys Ser Cys Ser Ser Trp Leu Asp Lys Glu Cys Val Tyr Phe Cys His
1               5                   10                  15

Leu Asp Ile Ile Trp
            20

(2) INFORMATION FOR SEQ ID NO:3:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:3:

Cys Thr Cys Phe Thr Tyr Lys Asp Lys Glu Cys Val Tyr Tyr Cys His
1               5                   10                  15

Leu Asp Ile Ile Trp
            20

(2) INFORMATION FOR SEQ ID NO:4:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO

```
        (iv) ANTI-SENSE:  NO (v) FRAGMENT TYPE:  internal (vi) ORIGINAL SOURCE:

(xi) SEQUENCE DESCRIPTION:  SEQ ID NO:4:

Cys Ser Ala Ser Ser Leu Met Asp Lys Glu Ala Val Tyr Phe Cys His
1               5                  10                  15

Leu Asp Ile Ile Trp
            20

(2) INFORMATION FOR SEQ ID NO:5:

(i) SEQUENCE CHARACTERISTICS:
             (A) LENGTH:  21 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  internal (vi) ORIGINAL SOURCE:

(xi) SEQUENCE DESCRIPTION:  SEQ ID NO:5:

Cys Ser Cys Asn Ser Trp Leu Asp Lys Glu Cys Val Tyr Phe Cys His
1               5                  10                  15

Leu  Asp  Ile  Ile  Trp
               20

(2) INFORMATION FOR SEQ ID NO:6:

(i) SEQUENCE CHARACTERISTICS:
             (A) LENGTH:  21 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  internal (vi) ORIGINAL SOURCE:

(xi) SEQUENCE DESCRIPTION:  SEQ ID NO:6:

Cys Ser Cys Lys Asp Met Thr Asp Lys Glu Cys Leu Asn Phe Cys His
1               5                  10                  15

Gln Asp Val Ile Trp
            20

(2) INFORMATION FOR SEQ ID NO:7:

(i) SEQUENCE CHARACTERISTICS:
             (A) LENGTH:  21 amino acids
             (B) TYPE:  amino acid
             (C) STRANDEDNESS:  single
             (D) TOPOLOGY:  linear (ii) MOLECULE TYPE:  peptide
```

(iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

Ala Ser Cys Ser Ser Leu Met Asp Lys Glu Cys Val Tyr Phe Ala His
1               5                  10                  15

Leu Asp Ile Ile Trp
            20

(2) INFORMATION FOR SEQ ID NO:8:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

Ala Ser Ala Ser Ser Leu Met Asp Lys Glu Ala Val Tyr Phe Ala His
1               5                  10                  15

Leu Asp Ile Ile Trp
            20

(2) INFORMATION FOR SEQ ID NO:9:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:9:

Cys Ser Cys Ser Ser Trp Leu Asp Lys Glu Ala Val Tyr Phe Ala His
1               5                  10                  15

Leu Asp Ile Ile Trp
            20

(2) INFORMATION FOR SEQ ID NO:10:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide

```
        (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

Cys Val Tyr Phe Cys His Leu Asp Ile Ile Trp
1               5                  10

(2) INFORMATION FOR SEQ ID NO:11:

(i) SEQUENCE CHARACTERISTICS:
              (A) LENGTH: 16 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:11:

Leu Met Asp Lys Glu Ala Val Tyr Phe Ala His Leu Asp Ile Ile Trp
1               5                  10                  15

(2) INFORMATION FOR SEQ ID NO:12:

(i) SEQUENCE CHARACTERISTICS:
              (A) LENGTH: 6 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

His Leu Asp Ile Ile Trp
1               5

(2) INFORMATION FOR SEQ ID NO:13:

(i) SEQUENCE CHARACTERISTICS:
              (A) LENGTH: 5 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal
```

```
        (vi) ORIGINAL SOURCE:

(xi) SEQUENCE DESCRIPTION:  SEQ ID NO:13:

Trp Asp Pro Val Leu
1               5

(2) INFORMATION FOR SEQ ID NO:14:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  internal (vi) ORIGINAL SOURCE:

(xi) SEQUENCE DESCRIPTION:  SEQ ID NO:14:

Glu Ala Ile Leu Trp
1               5

(2) INFORMATION FOR SEQ ID NO:15:

(i) SEQUENCE CHARACTERISTICS:
            (A) LENGTH:  7 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:

(xi) SEQUENCE DESCRIPTION:  SEQ ID NO:15:

Gly His Leu Asp Ile Ile Trp
1               5
```